(12) United States Patent
Lichtenstein et al.

(10) Patent No.: US 10,980,737 B1
(45) Date of Patent: Apr. 20, 2021

(54) SYSTEM FOR TREATING UNWANTED TISSUE USING HEAT AND HEAT ACTIVATED DRUGS

(71) Applicants: Samuel Victor Lichtenstein, Vancouver (CA); Daniel Gelbart, Vancouver (CA)

(72) Inventors: Samuel Victor Lichtenstein, Vancouver (CA); Daniel Gelbart, Vancouver (CA)

( * ) Notice: Subject to any disclaimer, the term of this patent is extended or adjusted under 35 U.S.C. 154(b) by 400 days.

(21) Appl. No.: 15/452,712

(22) Filed: Mar. 7, 2017

Related U.S. Application Data

(60) Provisional application No. 62/305,042, filed on Mar. 8, 2016.

(51) Int. Cl.
| | | |
|---|---|---|
| *A61K 9/00* | (2006.01) | |
| *A61M 31/00* | (2006.01) | |
| *A61M 16/14* | (2006.01) | |
| *A61B 18/14* | (2006.01) | |
| *A61K 45/06* | (2006.01) | |
| *A61B 18/00* | (2006.01) | |

(52) U.S. Cl.
CPC ............ *A61K 9/0004* (2013.01); *A61B 18/14* (2013.01); *A61K 9/007* (2013.01); *A61K 9/0019* (2013.01); *A61K 9/0053* (2013.01); *A61K 45/06* (2013.01); *A61M 16/14* (2013.01); *A61M 31/00* (2013.01); *A61B 2018/00541* (2013.01); *A61B 2018/00577* (2013.01); *A61M 2205/368* (2013.01)

(58) Field of Classification Search
CPC .. A61K 9/0004; A61K 9/0019; A61K 9/0053; A61K 9/007; A61K 45/06; A61B 18/14; A61B 2018/00541; A61B 2018/00577; A61M 16/14; A61M 31/00; A61M 2205/368

See application file for complete search history.

(56) References Cited

U.S. PATENT DOCUMENTS

| | | |
|---|---|---|
| 3,927,557 A | 12/1975 | Viertl |
| 4,298,009 A | 11/1981 | Mezrich et al. |
| 4,632,127 A | 12/1986 | Sterzer |
| 5,010,897 A | 4/1991 | Leveen |
| 5,117,829 A | 6/1992 | Miller et al. |

(Continued)

OTHER PUBLICATIONS

The BSD-2000/3D/MR http://www.pyrexar.com/hyperthermia/bsd-2000-3d RF Therapeutic Hyperthermia.

*Primary Examiner* — Manuel A Mendez

(57) ABSTRACT

The invention can selectively heat a diseased area in the lung while minimizing heating to the healthy area and surrounding tissue. This is done by exposing the lung to an electromagnetic field causing dielectric or eddy current heating. The invention is particularly useful for treating emphysema as the diseased areas have reduced blood flow. The diseased area will heat up rapidly while the healthy tissue will be cooled by the blood flow. This is particularly effective for treating emphysema because of the low mass of the lungs and the high blood flow. To avoid heating of surrounding organs the direction of the electromagnetic energy is switched in a way it always passes through lungs but only intermittently passes through adjacent organs. If heat activated drugs are present in the lungs, they are selectively released in the heated tissue.

20 Claims, 4 Drawing Sheets

(56) References Cited

U.S. PATENT DOCUMENTS

| | | | |
|---|---|---|---|
| 5,451,221 A | 9/1995 | Cho et al. | |
| 5,571,154 A | 11/1996 | Ren | |
| 6,328,689 B1 | 12/2001 | Gonzalez et al. | |
| 6,428,532 B1 | 8/2002 | Doukas et al. | |
| 6,610,043 B1 | 8/2003 | Ingenito | |
| 6,613,005 B1 | 9/2003 | Friedman et al. | |
| 6,692,494 B1 | 2/2004 | Cooper et al. | |
| 6,708,401 B2 | 3/2004 | Miyakawa et al. | |
| 6,712,816 B2 | 3/2004 | Hung et al. | |
| 6,997,918 B2 | 2/2006 | Soltesz et al. | |
| 7,004,940 B2 | 2/2006 | Ryan et al. | |
| 7,300,428 B2 | 11/2007 | Ingenito | |
| 7,412,977 B2 | 8/2008 | Fields et al. | |
| 7,587,230 B2 | 9/2009 | Litovitz | |
| 7,770,584 B2 | 8/2010 | Danek et al. | |
| 8,444,635 B2 | 5/2013 | Lictenstein | |
| 2003/0018327 A1 | 1/2003 | Truckai | |
| 2004/0047855 A1 | 3/2004 | Ingenito | |
| 2004/0147915 A1* | 7/2004 | Hasebe | A61M 25/10 606/28 |
| 2005/0038339 A1 | 2/2005 | Chauhan | |
| 2005/0085801 A1 | 4/2005 | Cooper et al. | |
| 2005/0281800 A1 | 12/2005 | Gong | |
| 2006/0047291 A1 | 3/2006 | Barry | |
| 2006/0135947 A1 | 6/2006 | Soltesz et al. | |
| 2006/0161233 A1 | 7/2006 | Barry et al. | |
| 2006/0259103 A1 | 11/2006 | Stenzel | |
| 2007/0043350 A1 | 2/2007 | Soltesz et al. | |
| 2008/0033412 A1 | 2/2008 | Whelan | |
| 2008/0097139 A1 | 4/2008 | Clerc et al. | |
| 2008/0132826 A1 | 6/2008 | Shadduck | |
| 2008/0167555 A1 | 7/2008 | Qian | |
| 2008/0228137 A1 | 9/2008 | Aljuri et al. | |
| 2008/0249503 A1 | 10/2008 | Fields | |
| 2010/0042020 A1 | 2/2010 | Ben-Ezra | |
| 2010/0125225 A1 | 5/2010 | Gelbart | |
| 2010/0125271 A1* | 5/2010 | Lichtenstein | A61B 18/18 606/41 |
| 2012/0089209 A1 | 4/2012 | Schoenbach et al. | |
| 2012/0310140 A1* | 12/2012 | Kramer | A61K 9/0009 604/20 |

* cited by examiner

SYSTEM FOR TREATING UNWANTED TISSUE USING HEAT AND HEAT ACTIVATED DRUGS

FIELD OF THE INVENTION

The invention relates to the medical field and in particular to the treatment of unwanted tissue.

BACKGROUND OF THE INVENTION

In many diseases it is desired to destroy or affect a non-desired tissue without harming the adjacent normal tissue. A non surgical approach has many advantages, such as shorter recovery time. Common non surgical approaches are:

Radiation therapy using X-ray or radioactive materials.
RF or microwave ablation using a probe applied from the outside or inside of the body, with or without cooling.
Use of drugs that selectively attach themselves or act on the malignant tissue.

In a patient suffering from emphysema, the diseased parts can not easily ventilate through the bronchi and trachea, thus preventing the lung from fully deflating and inflating. The trapped air does not allow the diaphragm to move up and down naturally. If the diseased area can be mildly heated such as to induce ablation, fibrosis or another mechanism to reduce volume, this would enable healthy tissue to fill the void and regenerate lung function. Another optional mechanism involves pneumothorax: upon heating the diseased area its ability to produce a surfactant coating and other chemicals can be to greatly reduced. This makes it possible to collapse the diseased area by collapsing the whole lung and re-inflating it. The healthy tissue will inflate while the diseased area will stay as a compressed lump. This will allow the diaphragm to move naturally and force air in and out of the healthy lung tissue. This procedure is well known in pulmonary medicine. Background on lung disease can be found in medical textbooks, such as "Pulmonary Pathophysiology" by Dr. John B. West, ISBN 0-683-08934-X. Prior art approaches to heat the diseased parts of the lung involve inserting an ablation device through the trachea and bronchi. This approach has two major shortcomings: only a small part of the lung is accessible, and precise mapping of the diseased area is required, as well as precise location of the ablation device. It is desired to have a system that automatically heats the diseased area without having to locate then precisely. It is also desired to be able to heat all diseased parts of the lung without excessively heating the healthy parts or the surrounding tissue. These and other objectives are achieved by the present invention.

SUMMARY OF THE INVENTION

The invention can selectively heat a diseased area in the lung while minimizing heating to the healthy area and surrounding tissue. This is done by exposing the lung to an electromagnetic field causing dielectric or eddy current heating. The invention is particularly useful for treating emphysema as the diseased area(s) have reduced blood flow. The diseased area(s) will heat up rapidly while the healthy tissue will be cooled by the blood flow. This is particularly effective for treating emphysema because of the low mass of the lungs and the high blood flow. To avoid heating of surrounding organs the direction of the electromagnetic energy is switched in a way it always passes through lungs but only intermittently passes through adjacent organs. If heat activated drugs are present in the lungs, they are selectively released in the heated tissue.

DETAILED DISCLOSURE

Figure 1:
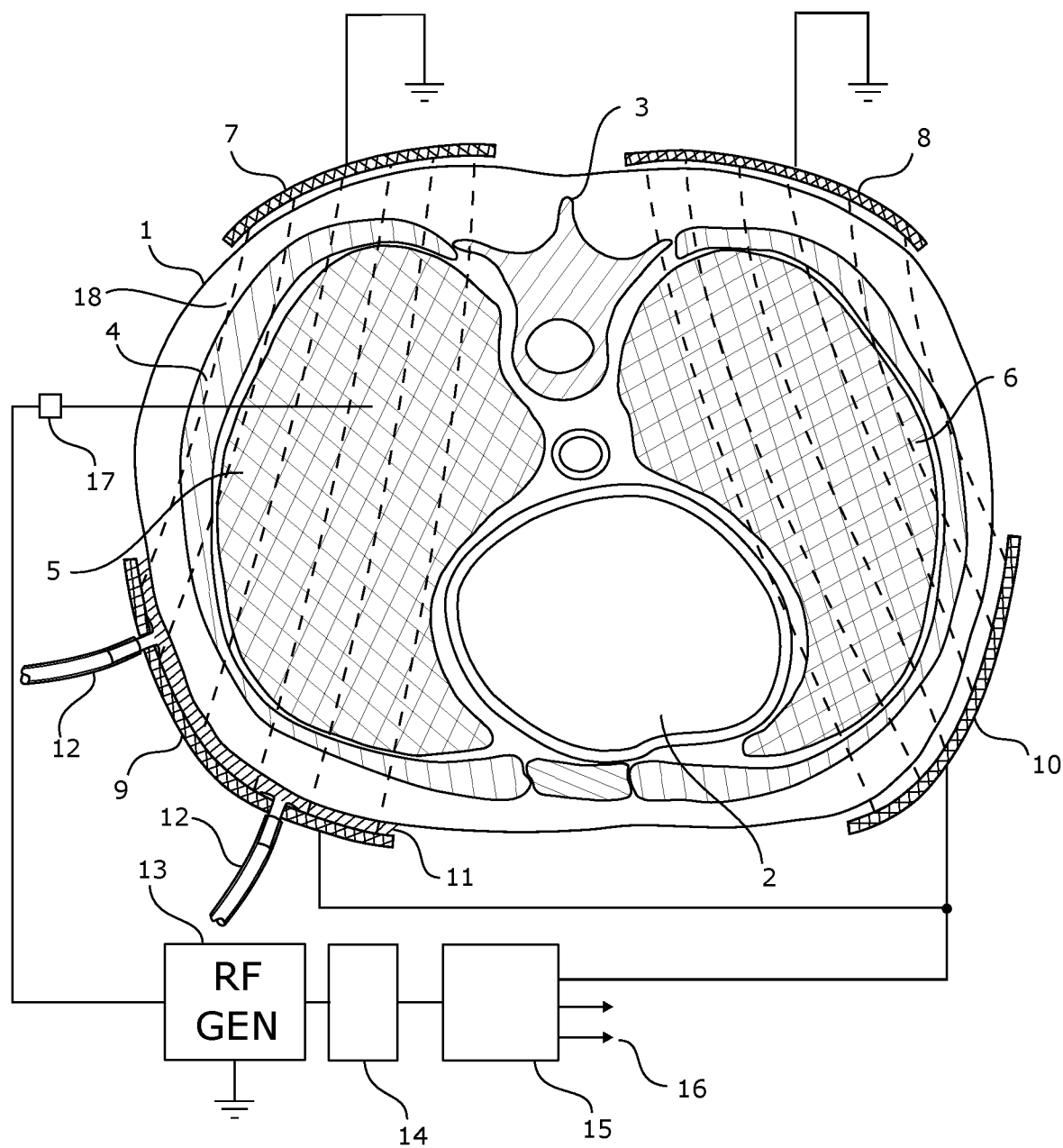
FIG. 1 is a cross section of a patient's chest being exposed to an electromagnetic field.

One aspect of the invention uses the fact that healthy lung tissue has much larger blood circulation than diseased tissue such as a lung affected by emphysema. When a non-contact heat source, such as radio-frequency (RF) energy, is directed at the lung the heat will be carried away from the healthy tissue by the blood flow while the diseased parts of the lung will heat up. When diseased tissue is heated up to around 60 deg C. it can lose the ability to expand back after lungs are collapsed (pneumothorax), because of damage to the surfactant layer and other physiological reasons. Causing the areas affected by emphysema to collapse prevents them from interfering with normal operation of the healthy parts of the lung, similar to what can be achieved by surgically removing the diseased part. Other mechanisms may exist that do not require pneumothorax: the heated diseased area can lose volume through ablation, fibrosis or other mechanisms and allow healthy lung tissue to fill the voids. The reason this procedure is effective on the lungs is that the mass of the lungs is low (about 1 Kg) while the blood flow through the lung is high (about 5 Kg/minute) and the blood flow tends to equalize the temperature of the healthy part of the lung with the rest of the body, representing a heat-sink of tens of kilograms. When lungs are exposed to a form of energy causing heating, such as RF or microwave, the amount of heating will be proportional to the heat-sinking mass. For a diseased lung it is typically below one Kg while for a healthy lung the heat transfer to the body represents a heat sink from 10 to 100 times larger. Based on this, when the diseased area will heat up to 50-70 degrees C., the healthy lung areas will only heat up a few degrees above normal body temperature. Another advantage of the method is that the location of the diseased area does not need to be precisely known: the heating energy can be directed at the whole lung, but only the diseased areas will heat up significantly. To assist in keeping down the temperature of the healthy parts of the lung, the patient can be breathing chilled air during the procedure. The diseased parts will not get a sufficient amount of chilled air to keep them cool. In one embodiment of the invention further treatment would not be necessary as the treatment will achieve sufficient volume reduction via fibrosis, ablation or other processes. In another embodiment, the treatment would need to be repeated several times over the course of days, weeks or months. In yet another embodiment, pneumothorax would be required to complete the process: after heating the lung, an operation than can take seconds or minutes, the lung can be collapsed by inserting a hypodermic needle into the pleural space, in order to allow air to leak into this space. Supplying the lung with pure oxygen will speed up the collapse as it is fully absorbed in the blood. After leaving the lung in a collapsed state long enough to allow the diseased area to collapse into a small volume, the lung is re-inflated by evacuating the pleural space via the same needle used to collapse the lungs. Obviously the procedure can be done on one lung at a time, as the patient can breathe with remaining lung. The procedure of collapsing and inflating the lung is done routinely in pulmonary medicine and need not be detailed here. This procedure can increase the effectiveness of the invention but is not a necessary part of it.

In FIG. 1 lungs 5 and 6 are surrounded by rib cage 4 inside the patient's body 1. In order to heat lungs 5 and 6 while minimizing heat to adjacent organs like heart 2 and spine 3, extracorporeal electrodes 7,8, 9 and 10 are carefully placed to create an electric field 18 covering as much of the lung as possible while minimizing penetration into adjacent organs. Fortunately, the human anatomy allows such a placement. To improve electrical coupling to the body while cooling it, a saline solution 11 and be introduced by tubes 12. Such a liquid coupling greatly improves the consistency of the coupling of the RF energy and the body. The solution is typically about 1% NaCl in water.

RF generator 13 supplies RF energy to the electrodes via an impedance matching network 14 and electrode selector 16, supplying energy to multiple electrodes via wires 16. The power of RF generator 13 is typically 1-5 KW at a frequency of 10-100 Mhz. It is desirable to choose frequencies in the ISM bands of the spectrum, such as 13.56 MHz. Since the output impedance of the generator is typically 50 Ohms and the body impedance is complex, impedance matching network 14 is required. Such a network is well known in the art and for the current invention involved a series capacitor followed by a parallel inductor. The values of the capacitor and inductor are determined after measuring the resistance and capacitance between the electrodes touching the body. To avoid resistive currents going through the body, and for electrical safety, it is desired to coat electrodes 7, 8, 9, 10 with a very thin layer of an insulating material. In testing the invention on rats, a 25 um layer of self-adhesive Kapton tape was used. The tape does not attenuate the capacitive currents much because it is very thin, therefore allowing high capacitance between electrode and the body. In order to minimize heating to adjacent organs the direction of the electromagnetic field is switched around, but it is always made to pass through the lungs. This can be achieved by moving around the energy source in order for the heating to arrive from different directions, or by electrode switching. If all these directions pass through the lung, the diseased lung area will be heated continuously while the surrounding tissue will be heated intermittently. A similar method is employed today in radiation therapy for cancer, however using heat energy has a significant advantage: the effect or radiation, such as X-ray or radioactivity, is cumulative while the effect of heating is non-cumulative. Heating a tissue by 30 degrees will permanently change it, while heating it 10 times by 3 degrees will have no effect. In the case of radiation the effect will be cumulative.

The heating process can be done open-loop (i.e. based on a previous experimental calibration of power and duration), or can be done using sensing or even close loop control. It was found out that the best sensors to sense the temperature inside the lung during the procedure were miniature glass encased thermistors such as Digikey part number 495-5820-ND. Such a thermistor 17 can control the RF power of generator 13 and stop the RF power when the correct ablation temperature was reached, typically 55-65 degrees C.

Figure 2:
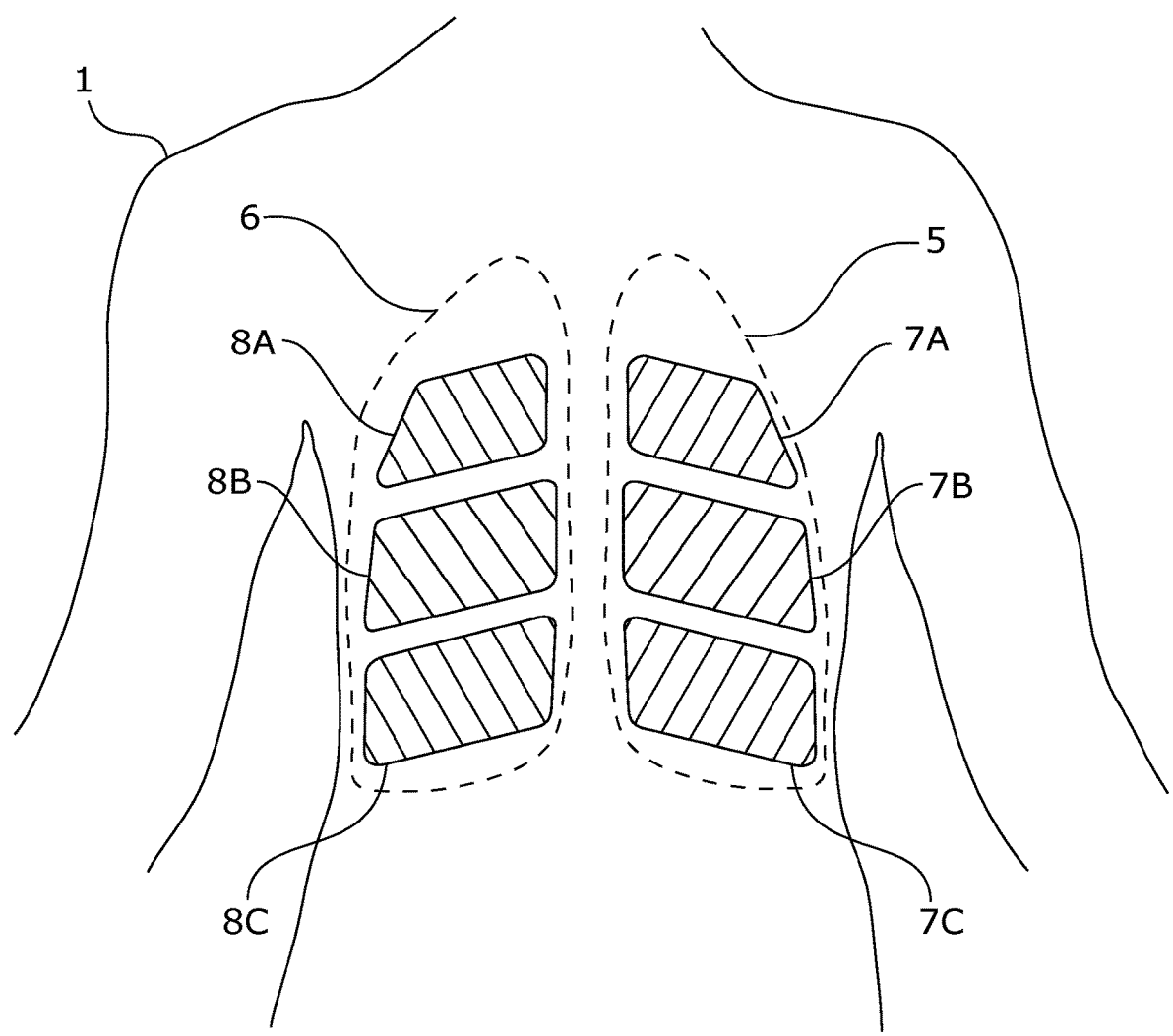
FIG. 2 is a view of the electrodes on the patient's back.

Referring now to FIG. 2, an example of electrode placement suitable for implementing electrode switching is shown. Three sets of electrodes 7A-8A, 7B-7B and 7C-8C are shown. As mentioned earlier, feeding a saline solution between electrodes and the skin of the patient greatly improves the effectiveness of the invention.

Figure 3:
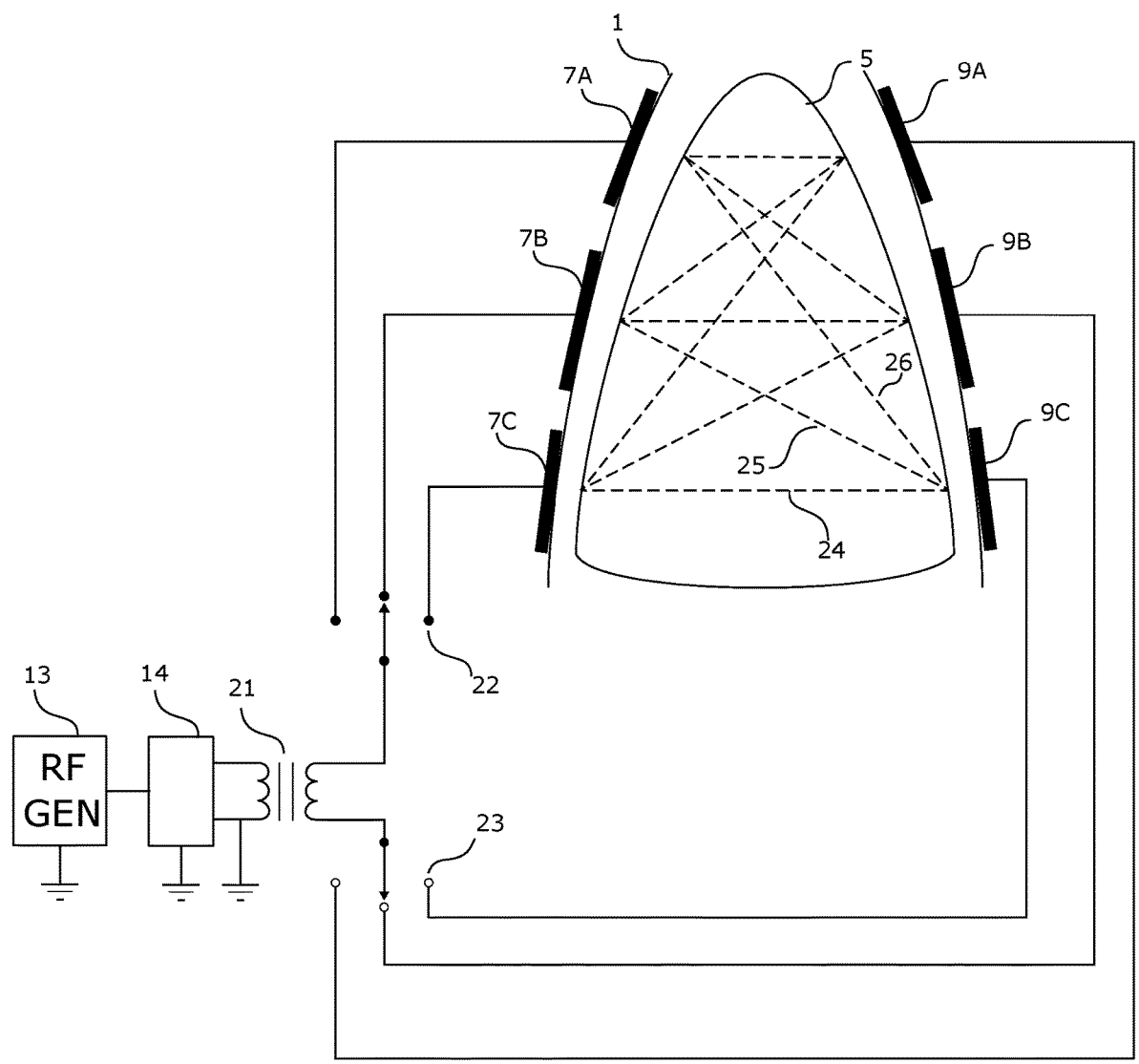
FIG. 3 is a side view of the patient, showing a method of electrode switching.

Referring now to FIG. 3 an example of electrode switching is shown. FIG. 3 is a side view of the patient. Choosing electrode 9C as an example, the electromagnetic field can be directed to electrodes 7A, 7B or 7C as shown by field lines 24, 25 and 26. To direct the field the electrodes are switched, in pairs, by electronic commutators 22 and 23. If a balanced configuration is desired the impedance matching network requires a balanced output (balanced relative to ground potential) which is easily done by transformer 21. Switches 22 and 23 can be solid state switches such as RF FET transistors or RF relays. The switching frequency, by way of example, is low and electrodes are switched every 30 to 300 seconds to allow the lung are along the path to heat up.

Figure 4:
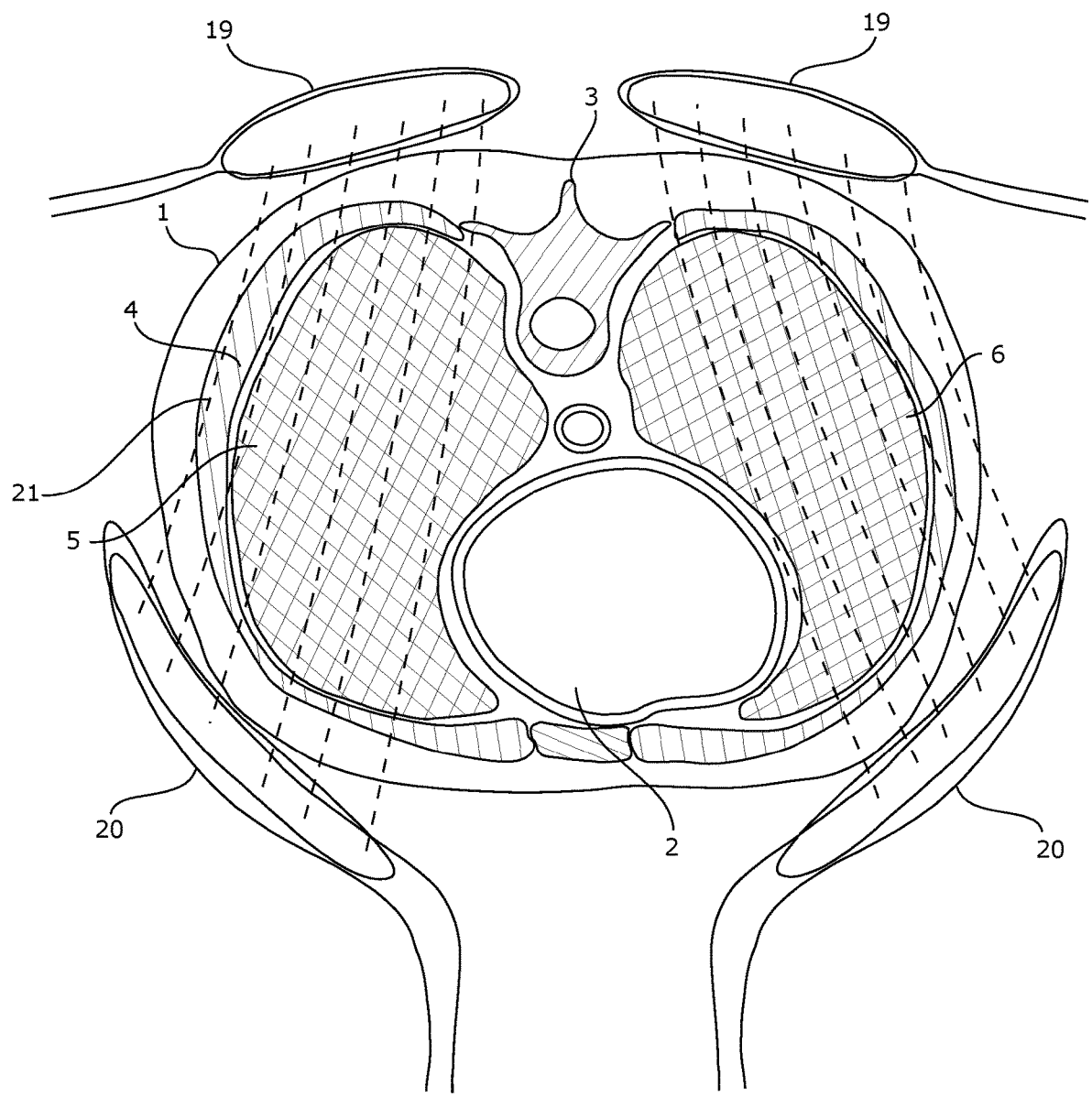
FIG. 4 is a cross section of a patient's chest being exposed to an electromagnetic field being generated by coils.

It is well known in the art of electromagnetism that an electromagnetic field contains both an electric field and a magnetic field. Any alternating electric field creates an alternating magnetic field and vice versa, however the heating mechanism can be dielectric heating, i.e. mainly responding to the electric field or can be mainly eddy current heating, the eddy currents induced by a changing magnetic field. For dielectric heating, the electrode arrangement shown in FIGS. 1, 2 and 3 are used. For Eddy current and mainly magnetic field induced heating the electrodes are replaced by RF coils, as shown in FIG. 4. The polarity of coils 19 and 20 is selected to create magnetic field lines 21 going through the lungs. Multiple coils can be used in a coil switching arrangement similar to the disclosed electrode switching arrangements disclosed earlier. The magnetic field can be further directed by using ferrite blocks. In the tests conducted on rats the dielectric heating was more effective than the magnetic field induced heating, but there may be unique benefits to each one of them.

The system was tested on several rats with induced emphysema in one of the lungs. The parameters used were:
  RF power of 100 W at 13.56 MHz.
  Series C parallel L matching network with saline irrigated electrodes.
  Reflected power was under 5%. Each electrode was approximately 25×50 mm, coated with 25 µm Kapton tape. Rats were shaved in contact area.
  Heating time was about 100 seconds. The healthy lung reached about 41 degrees C., while the areas with emphysema reached about 55 degrees C. All rats survived the treatment. Subsequent autopsy verified scar tissue in the areas of induced emphysema.

One or more heat activated drugs can be introduced into the patient to aid the process of neutralizing the diseased regions of the lung. These drugs are activated at the higher temperatures in the diseased lung regions when the invention in applied to the lung tissue. These drugs are not activated at typical body temperatures.

For example, these drugs can activate above 45 degrees Celcius, and therefore not affect the healthy lung tissue which does not reach 45 degrees Celcius. Non-limiting examples of the types of drugs that can be used in this application are drugs that become a strong toxin when activated.

For a list of non-limiting methods of drug delivery, the following are provided:
  1. Breathing a gas or aerosol. Gases are typically significantly more active at higher temperatures. In this case, the size of the drug carrying the particles can be very small, below 1 um. These particles enter the lungs, where they are released to treat the diseased tissue when heated to a temperature higher than the typical body temperature using the proposed invention.
2. The heat activated drugs can be delivered intravenously or through the patient's blood stream.
3. The heat activated drugs can be delivered orally.

If the drug or drugs are not naturally heat activated, it can be delivered in heat activated encapsulations. Non-limiting examples are:
1. The drug is micro-encapsulated by a water soluble material that melts at a low temperature. For example, the melting point of mixtures containing gels such as gelatin or agar can be formulated to melt at any temperature from 35 deg C. to 85 deg C. In healthy tissue, the encapsulation will dissolve slowly, releasing the drug at a low concentration and will be removed from the body over time. The drug will be rapidly activated in the heated area, immediately releasing most of the drug.
2. Similar to example 1, above, but the drugs are mixed into a gel mixture rather than being micro-encapsulated. The drug is only released if the mixture melts, otherwise released very slow as particles are absorbed and metabolized.
3. The drug is synthesized in a reaction between two or more components during the heat activation process. Each component is mixed into a gelatin/agar carrier. When the carrier melts, the components will react and create the active drug.

We claim:

1. A system for treating undesired tissue by radio frequency heating that comprises:
a heat activated drug or drugs present in a patient's lung;
an extracorporeal source to heat said undesired tissue;
wherein said heating source is from one or more extracorporeal radio frequency carrying coils surrounding the patient; and
said drug or drugs are activated at a higher temperature in a diseased region of the lung, but not at a lower temperature in a healthy region of the lung.

2. A system as in claim 1, wherein said drug or drugs are activated at a temperature above 45 degrees Celsius.

3. A system as in claim 1, wherein said drug or drugs are administered via a patient's blood stream.

4. A system as in claim 1, wherein said drug or drugs are administered via an air supply.

5. A system as in claim 1, wherein said drug or drugs are administered orally.

6. A system as in claim 1, wherein said drug or drugs become a strong toxin when activated.

7. A system as in claim 1, wherein a non-heat activated drug or drugs are made to be heat activated by encapsulating said non-heat activated drugs in a water soluble material that melts at the higher temperature in the diseased region of the lung but not at the lower temperature in the healthy region of the lung.

8. A system as in claim 1, wherein a non-heat activated drug or drugs are made to be heat activated by mixing said non-heat activated drugs into a gel mixture that melts at the higher temperature in the diseased region of the lung but not at the lower temperature in the healthy region of the lung.

9. A system as in claim 1, wherein said drug or drugs are made to be heat activated by synthesizing the drug from two or more components that are mixed into a gel carrier that melts at the higher temperature in the diseased region of the lung but not at the lower temperature in the healthy region of the lung.

10. A system as in claim 1 wherein said lower temperature in adjacent organs is created with the one or more extracorporeal radio frequency carrying electrodes by switching direction of produced electromagnetic energy in a way such that said electromagnetic energy always passes through a diseased region or regions of the lung, but only intermittently passes through adjacent regions.

11. A method for treating undesired tissue by applying radio frequency heating from an extracorporeal source to said tissue and activating a heat activated drug or drugs present in a patient's lung:
wherein said drug or drugs are activated at a higher temperature in a diseased region of the lung, but not at a lower temperature in a healthy region of the lung or adjacent organs; and
the radio frequency heating is from one or more extracorporeal radio frequency carrying coils surrounding the patient.

12. A method as in claim 11, wherein said drug or drugs are activated at a temperature above 45 degrees Celsius.

13. A method as in claim 11, wherein said drug or drugs are administered via a patient's blood stream.

14. A method as in claim 11, wherein said drug or drugs are administered via an air supply.

15. A method as in claim 11, wherein said drug or drugs are administered orally.

16. A method as in claim 11, wherein said drug or drugs become a strong toxin when activated.

17. A method as in claim 11, wherein a non-heat activated drug or drugs are made to be heat activated by encapsulating said non-heat activated drugs in a water soluble material that melts at the higher temperature in the diseased region of the lung but not at the lower temperature in the healthy region of the lung.

18. A method as in claim 11, wherein a non-heat activated drug or drugs are made to be heat activated by mixing said non-heat activated drugs into a gel mixture that melts at the higher temperature in the diseased region of the lung but not at the lower temperature in the healthy region of the lung.

19. A method as in claim 11, wherein said drug or drugs are made to be heat activated by synthesizing the drug from two or more components that are mixed into a gel carrier that melts at the higher temperature in the diseased region of the lung but not at the lower temperature in the healthy region of the lung.

20. A method as in claim 11 wherein said lower temperature in adjacent organs is created with the one or more extracorporeal radio frequency carrying electrodes by switching direction of produced electromagnetic energy in a way such that said electromagnetic energy always passes through a diseased region or regions of the lung, but only intermittently passes through adjacent regions.

* * * * *